United States Patent [19]

Haeckel et al.

[11] 4,136,196
[45] Jan. 23, 1979

[54] HYPOGLYCAEMICALLY ACTIVE 2-(PHENYLALKYL- OR -ALKENYL HYDRAZONO)-PROPIONIC ACID DERIVATIVES

[75] Inventors: Rainer Haeckel; Michael Oellerich, both of Hanover; Ruth Heerdt, Mannheim-Feudenheim; Manfred Hübner, Ludwigshafen am Rhein; Hans Kühnle, Mannheim-Neuostheim, all of Germany

[73] Assignee: Boehringer Mannheim GmbH, Mannheim, Germany

[21] Appl. No.: 835,939

[22] Filed: Sep. 22, 1977

[30] Foreign Application Priority Data

Sep. 25, 1976 [DE] Fed. Rep. of Germany ....... 2643303
Jun. 10, 1977 [DE] Fed. Rep. of Germany ....... 2726210

[51] Int. Cl.² .................. A61K 31/195; C07C 101/28
[52] U.S. Cl. ............................ 424/319; 260/340.5 R; 260/558 H; 260/558 A; 560/34; 560/142; 424/282; 424/311; 424/324; 562/439
[58] Field of Search ............... 260/518 R, 518 A, 519, 260/340.5, 558 H, 558 A; 560/34, 142; 424/282, 311, 319, 324

[56] References Cited

U.S. PATENT DOCUMENTS 3,666,801  5/1972  Robinson .................. 260/518 R

OTHER PUBLICATIONS

Chemical Abstracts, vol. 42, col. 7290(h), (1948).
Adnitt, "Diabetes", vol. 17, pp. 628–633.
Wickstrom et al., "The Lancet" pp. 995–997 (11/7/1964).
Van Praag et al., "Clinica Chimica Acta", vol. 8, pp. 466–475, (1963).

*Primary Examiner*—Gerald A. Schwartz
*Attorney, Agent, or Firm*—Sprung, Felfe, Horn, Lynch & Kramer

[57] ABSTRACT

A 2-hydrazono-propionic acid derivative of the formula

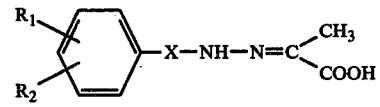

wherein
$R_1$ and $R_2$, each independently is hydrogen, halogen, trifluoromethyl, alkyl, hydroxyl, acyloxy or alkoxy or together are methylenedioxy, and
X is an aliphatic hydrocarbon radical containing 2–4 carbon atoms and is optionally substituted by an alkyl radical in the $\beta$- or $\gamma$-position to the nitrogen atom, or a physiologically compatible salt, ester or amide thereof, which exhibit hypoglycaemically activity.

8 Claims, No Drawings

HYPOGLYCAEMICALLY ACTIVE 2-(PHENYLALKYL- OR -ALKENYL HYDRAZONO)-PROPIONIC ACID DERIVATIVES

The present invention is concerned with new 2-(phenylalkylhydrazono)-propionic acid derivatives and with the preparation thereof.

It is known that some monoamino oxidase inhibitors, for example phenelzine (2-phenylethyl-hydrazine) and mebanazine (1-phenylethyl-hydrazine) can be hypoglycaemically active in high dosages (Adnitt, P.I., Hypoglycemic action of monoamino oxidase inhibitors, Diabetes, 17, 628–633/1968; Wickstrom, Pettersen, K., Treatment of diabetes with monoamino oxidase inhibitors, Lancet, 2, 995–997/1964).

However, the main action is the inhibition of the monoamino oxidases (MAO) so that these compounds have admittedly been used in the therapy of psychic illnesses (Van Praag, H. M., Leijnse, B., The influence of some antidepressant drugs of the hydrazine type on the glucose metabolism in depressed patients, Clin. Chim. Acta, 8, 466–475/1963) but could not be used as blood sugar-lowering medicaments.

It is an object of the present invention to provide new compounds which exhibit a hypoglycaemic activity at a dosage level at which an inhibition of monoamino oxidases does not occur or does not occur to a substantial degree.

Surprisingly, we have now found that hydrazones of pyruvic acid, which contain phenelzine or similar compounds as the hydrazine component, exhibit, in comparison with the corresponding hydrazines, a considerably increased hypoglycaemic activity, whereas the monoamino oxidase inhibition is practically completely suppressed.

Thus, according to the present invention, there are provided new propionic acid derivatives of the general formula:

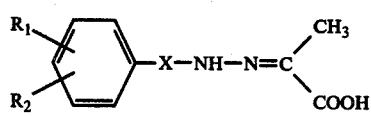 (I)

wherein $R_1$ and $R_2$, which can be the same or different, are hydrogen or halogen atoms, or trifluoromethyl, alkyl, hydroxyl, acyloxy or alkoxy radicals or together represent a methylenedioxy radical and X is a straight-chained, saturated or unsaturated aliphatic hydrocarbon radical containing 2 to 4 carbon atoms which is optionally substituted by an alkyl radical in the $\beta$- or $\gamma$-position to the nitrogen atom; and the physiologically compatible salts, esters and amides thereof.

By halogen atoms, there is to be understood fluorine, chlorine and bromine atoms; the alkyl and alkoxy radicals contain up to 3 carbon atoms and more preferably methyl or methoxy radicals, respectively. The acyloxy radicals are preferably alkanoyloxy of up to 4 to carbon atoms, the acetoxy radical being particularly preferred.

The new compounds of the general formula (I) can be prepared, for example, by reacting a hydrazine of the general formula:

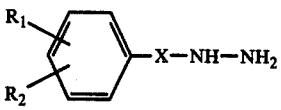 (II)

wherein $R_1$, and $R_2$ and X have the same meanings as above, or a salt thereof, with a propionic acid derivative of the general formula:

 (III)

wherein Y and Y', which can be the same or different, are halogen atoms or alkoxy radicals or together represent an oxygen atom and R' is a hydrogen atom or a lower alkyl radical, and subsequently, if desired, the product obtained is converted into a salt, ester or amide or the free acid is liberated from a derivative thereof.

In this process, the substituted hydrazine (II) or an appropriate salt thereof is mixed, in an appropriate polar solvent, for example water, a lower alcohol or acetic acid, with a propionic acid derivative (III) or, preferably, with a salt thereof and possibly adjusted to a weakly acidic pH value with the help of a buffer, for example sodium acetate. The reaction proceeds at ambient temperature but can also be carried out with heating. Since the hydrazone (I) is a sparingly soluble compound, it can be filtered off from the reaction mixture or it can be extracted with a non-polar solvent.

If desired, in a one-pot process, the substituted hydrazine (II) can be prepared, for example, from an appropriate amine with hydroxylamino-O-sulphonic acid and, after the addition of the propionic acid derivative (III), the desired hydrazone is precipitated out.

The physiologically compatible salts are, in particular, the alkali metal, alkaline earth metal and ammonium salts, as well as the salts with blood sugar-lowering biguanides. These salts can be prepared in the usual manner, for example by reaction with the corresponding free bases or carbonates.

The present invention also provides blood sugar-lowering compositions which may be in any of the forms of administration usual for oral and parenteral use, for example tablets, capsules, dragees, syrups, solutions, suspensions, drops, suppositories and the like. For this purpose, the active material is admixed with solid or liquid pharmaceutical diluents or carriers and then brought into the desired form. Solid carrier materials include, for example, starch, lactose, mannitol, methyl cellulose, talc, highly dispersed silicic acid, high molecular weight fatty acids (for example stearic acid), gelatine, agar-agar, calcium phosphate, magnesium stearate, animal and vegetable fats and solid high molecular weight polymers (for example polyethylene glycols). Compositions which are suitable for oral administration can, if desired, contain flavoring and/or sweetening materials.

As injection medium, it is preferred to use water which contains the additives usual in the case of injection solutions, such as stabilizing agents, solubilizing agents and/or buffers. Additives of this type include, for example, acetate and tartrate buffers, ethanol, complex forming agents (such as ethylenediamine-tetraacetic acid and the non-toxic salts thereof) and high molecular weight polymers (for example liquid polyethylene oxide) for viscosity regulation.

Preferred compounds according to the present invention include, in addition to those compounds mentioned in the specific examples, the following compounds and the physiologically compatible salts thereof:

2-[2-(m-tolyl)-ethylhydrazono]-propionic acid
2-(3-methoxyphenethylhydrazono)-propionic acid
2-(2-chlorophenethylhydrazono)-propionic acid
2-(4-phenylbutylhydrazono)-propionic acid
2-(5-chloro-2-methoxy-phenethylhydrazono)-propionic acid
2-(4-phenyl-2-butenylhydrazono)-propionic acid
2-(4-phenyl-3-butenylhydrazono)-propionic acid
2-(3-phenyl-butylhydrazono)-propionic acid
2-(3-phenyl-2-butenylhydrazono)-propionic acid
2-(2-methyl-3-phenyl-propylhydrazono)-propionic acid.

The following examples are given for the purpose of illustrating the present invention:

EXAMPLE 1

2-(Phenethylhydrazono)-propionic acid 23.6 g. Phenethylhydrazine sulphate are dissolved in 200 ml. water and mixed, while stirring at ambient temperature, with a solution of 8.8 g. pyruvic acid and 24.6 g. sodium acetate trihydrate in 70 ml. water. An oil initially separates out which crystallizes slowly. The product is filtered off with suction to give 20.0 g. of crude product. This product is recrystallized from 30 ml. toluene to give 18.7 g. (90.9% of theory) 2-(phenethylhydrazono)-propionic acid; m.p. 74°–76° C.

In an analogous manner, the following compounds are obtained by reacting pyruvic acid with
  a. 4-methoxyphenethylhydrazine hydrochloride to give 2-(4-methoxyphenethylhydrazono)-propionic acid; m.p. 101°–102° C., after recrystallization from toluene;
  b. 4-chlorophenethylhydrazine hydrochloride to give 2-(4-chlorophenethylhydrazono)-propionic acid; m.p. 87°–89° C., after recrystallization from isopropanol.
  The compound contains ½ mole of water;
  c. 2-(p-tolyl)-ethylhydrazine hydrochloride to give 2-[2-(p-tolyl)-ethylhydrazono]-propionic acid; m.p. 69°–70° C., after recrystallization from isopropanol/water;
  d. p-hydroxyphenethylhydrazine sulphate (m.p. 140°–144° C. (decomp.)) to give 2-(p-hydroxyphenethylhydrazono)-propionic acid; m.p. 138°–140° C. (decomp.);
  e. o-methylphenethylhdrazine hydrochloride to give 2-(2-methylphenethylhydrazono)-propionic acid; m.p. 92° C., after recrystallization from isopropanol/water;
  f. 4-fluorophenethylhydrazine hydrochloride (m.p. 180°–182° C.) to give 2-(4-fluorophenethylhydrazono)-propionic acid; m.p. 103°–104° C., after recrystallization from isopropanol/water; and
  g. 3-trifluoromethyl-phenethylhydrazine hydrochloride (m.p. 148°–149° C.) to give 2-(3-trifluoromethyl-phenethylhydrazono)-propionic acid; m.p. 64°–66° C., after recrystallization from isopropanol/water.

EXAMPLE 2

Ethyl 2-(phenethylhydrazono)-propionate 1.7 g. Phenethylhydrazine hydrochloride, 1.2 g. ethyl pyruvate and 0.8 g. sodium acetate are dissolved in 7 ml. water and 15 ml. glacial acetic acid. The reaction mixture is left to stand for 4 hours at ambient temperature and then 30 ml. water are added thereto. Ethyl 2-(phenethylhydrazono)-propionate separates out in the form of an oil. The reaction mixture is shaken out with diethyl ether and the ethereal extract is washed with an aqueous solution of sodium bicarbonate and then dried and evaporated. The residue, which does not crystallize, is analytically pure. There is obtained ethyl 2-(phenethylhydrazono)-propionate in a yield of 64% of theory.

EXAMPLE 3

Methyl 2-(phenethylhydrazono)-propionate 3.6 g. Phenethylhydrazine hydrochloride and 2.0 g. methyl pyruvate are dissolved in 20 ml. methanol and left to stand at ambient temperature for 30 minutes, followed by cooling to 0° C., whereafter 30 ml. water are added thereto. 2.8 g. (61% of theory) methyl 2-(phenethylhydrazono)-propionate crystallizes out; m.p. 59°–60° C. (decomp.).

EXAMPLE 4

2-(phenethylhydrazono)-propionamide 3.4 g. Phenethylhydrazine hydrochloride are dissolved in 10 ml. water and mixed with 1.7 g. pyruvamide dissolved in 50 ml. water. 2.1 g. sodium acetate trihydrate are added thereto and the reaction mixture well shaken up. 2-(Phenethylhydrazono)-propionamide crystallizes out. It is filtered off and recrystallized from a mixture of cyclohexane and toluene. The yield is 2.0 g. (50% of theory); m.p. 78° C. (decomp.).

EXAMPLE 5

Sodium 2-(3-phenylpropylhydrazono)-propionate 3 g. 3-Phenylpropylhydrazine hydrochloride are dissolved in 10 ml. water and a solution of 1.4 g. pyruvic acid and 2.1 g. sodium acetate in 5 ml. water added thereto, an oil being formed. The reaction mixture is further stirred for 2 hours and the aqueous solution is then poured off and the remaining oil is washed with water and dissolved in methylene chloride. After drying with anhydrous sodium sulphate, the methylene chloride is evaporated off and to the oily substance obtained (3.5 g.; 80% of theory) there is added a solution of sodium methylate prepared from 0.35 g. sodium in 20 ml. methanol. The methanol is evaporated off and the residue is stirred with diethyl ether. The sodium salt of 2-(3-phenylpropylhydrazono)-propionic acid separates out; m.p. 201°–203° C. Yield 2.4 g.; 62% of theory.

The following compounds are obtained in an analogous manner by reacting pyruvic acid with:
  a. cinnamylhydrazine hydrochloride and subsequent preparation of the sodium salt: sodium 2-(cinnamylhydrazono)-propionate; m.p. 210° C.
  b. 2-methoxyphenethylhydrazine hydrochloride (m.p. 108°–110° C.) and subsequent preparation of the sodium salt: sodium 2-(2-methoxyphenethylhydrazono)-propionate; m.p. 193°–195° C. (decomp.);
  c. β-methylcinnamylhydrazine hydrochloride (m.p. 148°–150° C.) and subsequent preparation of the sodium salt: sodium 2-(β-methylcinnamylhydrazono)-propionate; m.p. 170°-175° C. (sinters above 149° C.);

d. 2-phenylpropylhydrazine hydrochloride and subsequent preparation of the sodium salt: sodium 2-(2-phenylpropylhydrazono)-propionate; m.p. 188°-190° C.;

e. 3-bromophenethylhydrazine hydrochloride (m.p. 184°-185° C.) and subsequent preparation of the sodium salt: sodium 2-(3-bromophenethylhydrazono)-propionate; m.p. 190°-193° C. (decomp.), after recrystallization from isopropanol; and f. 3,4-methylenedioxy-phenethylhydrazine sulphate (m.p. 138°-140° C. (decomp.)) and subsequent preparation of the sodium salt: sodium 2-(3,4-methylenedioxy-phenethylhydrazono)-propionate; m.p. 175°-177° C. (decomp.), after recrystallization from ethanol.

EXAMPLE 6

2-(Phenethylhydrazono)-propionic acid 6 g. Ethyl 2-(phenethylhydrazono)-propionate (prepared according to Example 2) are dissolved in a solution of 1.4 g. potassium hydroxide in 28 ml. 80% ethanol and saponified at ambient temperature. After stirring for 30 hours, the reaction mixture is mixed with 25 ml. water and shaken out twice with 50 ml. amounts of diethyl ether. The aqueous phase is acidified with dilute hydrochloric acid. The crystals which precipitate out are filtered off and recrystallized from toluene. There is obtained 2-(phenethylhydrazono)-propionic acid in a yield of 47% of theory; m.p. 74°-76° C.

EXAMPLE 7

Sodium 2-(phenethylhydrazono)-propionate

A mixture of 24.2 g. phenethylamine, 9.8 g. potassium hydroxide and 50 ml water is heated to 70° C. and 4.4 g. pyruvic acid are added. A solution of 5.6 g. hydroxylamino-O-sulfonic acid in 20 ml water is added with stirring over 15 minutes and stirring at 70° C. continued for for another 15 minutes. The solution is cooled to ambient temperature, precipitated potassium sulfate is filtered off, and the still alkaline solution is extracted three times with ether. The solution is acidified with hydrochloric acid and the precipitated 2-(phenethylhydrazono)-propionic acid taken up in ether. The ethereal solution is dried with anhydrous sodium sulfate and evaporated. The residue is dissolved in 8 ml. ethanol, 30% sodium methylate solution and 20 ml ether are added. The crystallizing sodium 2-(phenethylhydrazono)-propionate is filtered off and washed with ether. m.p. above 300° C.

EXAMPLE 8

2-(Phenethylhydrazono)-propionic acid

To a solution of 5.7 g. 2,2-dichloropropionic acid and 2.8 g. potassium carbonate in 40 ml water is added a solution of 6.9 g. phenethylhydrazine hydrochloride and 5.6 g. potassium carbonate in 20 ml water. The mixture is heated with stirring to 90° C., a further solution of 5.6 g. potassium carbonate in 20 ml water is dropped in over 30 minutes and further stirred for 60 minutes at 90° C. Afterwards the still alkaline solution is cooled to ambient temperature, shaken out with ether and acidified with concentrated hydrochloric acid. 2-(phenethylhydrazono)-propionic acid crystallizes out and is recrystallized from toluene. The yield is 3.3 g. (40% of theory); m.p. 74°-76° C.

The novel compounds may be administered by themselves or in conjunction with carriers which are pharmacologically acceptable, either active or inert. The dosage units are about 0,2 to 2 grams per day for an adult or about 3–30 mg/kg per day although higher or lower dosages can be used. Rather than a single dose it is preferable if the compounds are administered in the course of a day, i.e., about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50–500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diaminetetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

As noted hereinabove the material administered may be the acid or a salt, ester or amide thereof. It is believed that due to hydrolysis in the body the active material is in all these instances the same, viz. probably the acid.

TEST PROTOCOL

In order to illustrate the pharmacological properties of the compounds according to the invention, the blood sugarlowering effect and the monoaminoxidase (MAO) inhibition were determined and compared with some corresponding hydrazines. The new compounds lower the blood sugar at a lower concentration than, and the MAO only at higher concentration than, the corresponding hydrazines, so that they are suitable as antidiabetics.

Conduction of the Blood Sugar Tests

Metabolically healthy, cross-bred, fasting guinea pigs were injected with the substances as aqueous solutions of their sodium salts, i.p. A control group receives equivalent amounts of an isotonic NaCl solution. Directly before, as well as in hourly intervals up to the fourth hour after the rejection, 10 μl blood are taken from an ear border vein and the blood glucose is determined by means of the trouble-free and specific hexokinase technique. That dosage is considered as threshhold dosage which significantly lowers the blood glucose concentration in comparison to the control group.

Measuring of the MAO Activity in Vitro

An unrefined MAO preparation is obtained by comminution of guinea pig liver or brain with the Ultraturrax and subsequent centrifuging at about 10,000 g. The liquid contains the MAO portion dissolved in the cytoplasm and is used for the activity measurements. As substrate there is used kynuramine whose oxidative decomposition by the MAO can be directly observed at 360 m μ in the photometer. The extinction decrease per time unit is a measure of the enzyme activity. The enzyme widely is tested with addition of various inhibitor concentrations and that concentration determined which effects a 50% inhibition of the initial MAO activity (inhibitor concentration = 0).

|  | Threshold i.p. Dosage for Hypoglycaemic Activity in Testing Guinea Pigs, mg/kg | Concentration for 50% MAO Inhibititions (Mol/ml) |
| --- | --- | --- |
| Sodium-2-(cinnamylhydrazono)-propionate | 15 | |
| Sodium-2-(3-phenylpropylhydrazono)-propionate | 35 | |
| 2-(phenethylhydrazono)-propionic acid ethyl ester | 25 | |
| 2-[2-(p-tolyl-ethylhydrazono]-propionic acid | 50 | |
| 2-(2-methylphenethylhydrazono)-propionic acid | 50 | |
| 2-(4-fluorophenethylhydrazono)-propionic acid | 25 | |
| 2-(phenethylhydrazono)-propionic acid | 15 | $0.6 \times 10^{-6}$ |
| 2-(4-chlorophenethylhydrazono)-propionic acid | 25 | |
| 2-(4-methoxyphenethylhydrazono)-propionic acid | 50 | |
| 2-(phenethylhydrazono)-propionamide | 50 | |
| Methyl 2-(phenethylhydrazono)-propionate | 50 | |
| Sodium-2-(β-methylcinnamylhydrazono)-propionate | 10 | |
| Sodium-2-(2-methoxyphenethylhydrazono)-propionate | 25 | |
| Sodium-2-(3-bromophenethylhydrazono)-propionate | 25 – 50 | |
| Comparison Compounds | | |
| 3-phenyl-propen-2-yl--hydrazin-hydrochloride | >50 | |
| Phenelzine | ≧50 | $0.4 \times 10^{-9}$ |

It will be appreciated that the instant specification and example are set forth by way of illustration and not limitation, and that various modifications and changes may be made without departing from the spirit and scope of the present invention.

What is claimed is:

1. A 2-hydrazono-propionic acid derivative of the formula:

$$R_1, R_2\text{-phenyl}-X-NH-N=C\begin{array}{c}CH_3\\COOH\end{array}$$

wherein
R₁ and R₂, each independently is hydrogen, halogen, trifluoromethyl, alkyl of up to 3 carbon atoms, hydroxyl, alkanoyloxy of up to 4 carbon atoms or alkoxy of up to 3 carbon atoms or together are methylene-dioxy, and X is an aliphatic hydrocarbon radical containing 2–4 carbon atoms and is optionally substituted by an alkyl radical of up to 3 carbon atoms in the β- or δ-position to the nitrogen atom, or a physiologically compatible salt, lower alkyl ester or amide thereof.

2. A compound according to claim 1, wherein
R₁ and R₂ each independently is hydrogen, fluorine, chlorine, bromine, trifluoromethyl, hydroxyl, alkyl or alkoxy of up to 3 carbon atoms, alkanoyloxy of up to 4 carbon atoms, or together represent a methylenedioxy radical, and X is is an aliphatic hydrocarbon radical containing 2–4 carbon atoms and is optionally substituted by an alkyl radical of up to 3 carbon atoms in the β- or γ-position to the nitrogen atom.

or a physiologically compatible salt, lower alkyl ester or amide thereof.

3. A compound according to claim 1, wherein such compound is 2-(phenethylhydrazono)-propionic acid of the formula

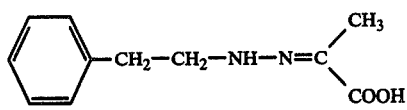

or a physiologically compatible salt thereof.

4. A compound according to claim 1, wherein such compound is 2-(cinnamylhydrazono)-propionic acid of the formula

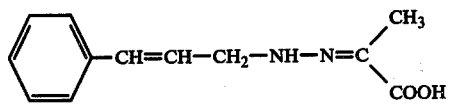

or a physiologically compatible salt thereof.

5. A compound according to claim 1, wherein such compound is 2(β-methylcinnamylhydrazono)-propionic acid of the formula

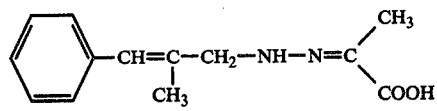

or a physiologically compatible salt thereof.

6. A hypoglycaemic composition of matter comprising a hypoglycaemically active amount of a compound according to claim 1 or a salt, ester or amide thereof in admixture with a diluent.

7. A method of lowering the blood sugar level of a patient comprising administering to such patient a hypoglycaemically active amount of a compound according to claim 1 or a salt, ester or amide thereof.

8. The method according to claim 1, wherein there is administered
    2-(phenethylhydrazono)-propionic acid,
    2-(cinnamylhydrazono)-propionic acid, or
    2-(β-methylcinnamylhydrazono)-propionic acid,
or a physiologically compatible salt thereof.

* * * * *

UNITED STATES PATENT AND TRADEMARK OFFICE
CERTIFICATE OF CORRECTION

PATENT NO. : 4,136,196
DATED : January 23, 1979
INVENTOR(S) : Haeckel et al

It is certified that error appears in the above-identified patent and that said Letters Patent are hereby corrected as shown below:

Col. 5, line 43      Cancel "for", second occurrence.

Col. 6, line 62      Cancel "sugarlowering", substitute --sugar lowering--.

Col. 8, line 16      Cancel "$\delta$", substitute --$\chi$--.

Signed and Sealed this

Third Day of July 1979

[SEAL]

Attest:

Attesting Officer

LUTRELLE F. PARKER
*Acting Commissioner of Patents and Trademarks*